United States Patent [19]
Gagnon et al.

[11] Patent Number: 5,902,459
[45] Date of Patent: May 11, 1999

[54] RECOVERY OF PRODUCTS FROM TOLUENEDIISOCYANATE RESIDUES

[75] Inventors: Steven D. Gagnon, Prairieville, La.; Sandy A. Bananto, Dearborn, Mich.

[73] Assignee: BASF Corporation, Mt. Olive, N.J.

[21] Appl. No.: 08/661,176

[22] Filed: Jun. 10, 1996

[51] Int. Cl.[6] .......................... B01D 3/34; C07C 249/14; C08G 18/08
[52] U.S. Cl. .............. 203/38; 203/98; 521/160; 560/358; 560/360
[58] Field of Search .................. 203/38, 59, 98, 203/DIG. 6; 521/160, 358, 360

[56] References Cited

U.S. PATENT DOCUMENTS

| | | | |
|---|---|---|---|
| 3,404,103 | 10/1968 | Matsudaira et al. | 521/49.5 |
| 3,658,656 | 4/1972 | Adica et al. | 203/49 |
| 3,729,386 | 4/1973 | Irwin et al. | 203/60 |
| 4,076,577 | 2/1978 | Hetzel et al. | 159/47.1 |
| 4,480,081 | 10/1984 | Rosin et al. | 528/49 |
| 4,654,443 | 3/1987 | Marks et al. | |
| 4,794,194 | 12/1988 | Burgoyne et al. | 560/360 |
| 5,281,629 | 1/1994 | Hoveaindt et al. | |
| 5,298,128 | 3/1994 | Hansdorf et al. | |
| 5,314,588 | 5/1994 | Zarnack et al. | 203/38 |
| 5,354,369 | 10/1994 | Shimomura et al. | 106/22 H |
| 5,498,780 | 3/1996 | Kubota et al. | |

FOREIGN PATENT DOCUMENTS

| | | |
|---|---|---|
| 122367 | 9/1981 | Japan . |
| 59-89321 | 5/1984 | Japan . |
| 155222 | 8/1985 | Japan . |
| 625575 | 2/1994 | Japan . |

OTHER PUBLICATIONS

Perry et al "Distillation", 1965, p. 3.
"Decomposition of Polyurethane Foams by Alkanolamines," Kanaya and Takahashi, *Journal of Applied Polymer Science*, vol. 51, pp. 675–682 (1994).
"Preparation of Epoxy Hardeners from Waste Rigid Polyurethane Foam and Their Application," S. Xue et al., *Journal of Applied Polymer Science*, vol. 56, pp. 127–134 (1995).

*Primary Examiner*—Virginia Manoharan
*Attorney, Agent, or Firm*—Fernando A. Borrego

[57] ABSTRACT

There is now provided a method of recycling toluenediisocyanate residue resulting from the production of toluenediisocyanate by the reaction of toluenediamine by phosgenation in the presence of a solvent. In accordance with the teachings of the present invention, the toluenediisocyanate residue is treated at reflux with an alkanolamine to obtain an intermediary product which is distilled thereby giving rise to various products including but not limited to at least one component selected from toluenediamine, oxazolidone and hydroxyethylimidiazolidone. Preferably the alkanolamine employed is a monoethanolamine.

2 Claims, No Drawings

RECOVERY OF PRODUCTS FROM TOLUENEDIISOCYANATE RESIDUES

FIELD OF THE INVENTION

The present invention relates to a process for recovering products from toluenediisocyanate residues resulting from the manufacture of toluenediisocyanates.

More particularly, the process relates to the recovery of various products such as toluenediamine, oxazolidone, hydroxyethylimidiazolidone, and methylbenzimidiazole by reacting toluenediisocyanate residues with an alkanolamine.

BACKGROUND OF THE INVENTION

Toluenediisocyanates, otherwise referred to herein as TDI have become an important component in the preparation of various commercially useful products including but not limited to, polyurethane foams, elastomers and coatings. However, as a results of the production of toluenediisocyanates, waste in the form of toluenediisocyanate residues, sometimes referred to as distillation bottoms, are generated.

In view of the extensive production of toluenediisocyanate world wide and in turn, the generation of high quantities of toluenediisocyanate residues, the need for a reliable process for recycling toluenediisocyanate residues and recovering the useful products generated as a result is readily apparent.

While alternative processes can be employed to recycle toluenediisocyanate residues into useful products, it is believed that the present invention offers the most convenient and cost effective alternative available to date. For example, it is possible to recover many of the aforementioned products from toluenediisocyanate residues by reacting the residue with an excess amount of an alcohol such as ethanol, propanol, butanol, pentanol and cyclopentanol, among others. However, in order to drive the reaction, the residue must be heated to a temperature of approximately 200° C. As a result of the reaction, an extensive amount of carbon dioxide is generated, thus, the reaction must be carried out in a pressure vessel capable of handling pressures of up to 400 lbs/in$^2$. In contrast, the process of the present invention does not generate any carbon dioxide, or other such gases and therefore, can be carried out at relatively low pressures.

SUMMARY OF THE INVENTION

The present invention, therefore, relates to a process for recycling toluenediisocyanate residue generated during the production of toluenediisocyanates comprising the steps of a) treating toluenediisocyanate residue with an alkanolamine and heating at reflux to produce an intermediary component; and b) distilling the intermediary to obtain one or more useful products.

More particularly, the present invention relates to a process for recovering one or more products including, for example toluenediamine, oxazolidone and hydroxyethylimidiazolidone from toluenediisocyanate residues by reacting therewith an alkanolamine such as monoethanolamine at reflux. The toluenediamine recovered can be used for various purposes including the further production of toluenediisocyanate.

As should be understood by those skilled in the art, the process of the present invention, thus, not only offers a preferred alternative to the disposal of toluenediisocyanate residues, but also offers a process for generating various useful end products.

DETAILED DESCRIPTION OF THE PREFERRED EMBODIMENT

As noted, toluenediisocyanate is utilized in a vast array of compositions useful for forming numerous commercial products, such as polyurethane foams, elastomers and coatings, among others. To prepare high volumes of toluenediisocyanates (TDI) and, consequently a substantial quantity of toluenediisocyanate residue, toluenediamine is phosgenated according to the following reaction scheme in the presence of a suitable solvent.

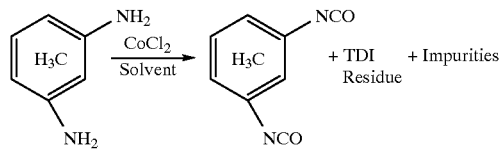

As a result of the production of toluenediisocyanate by the reaction scheme shown above, approximately 2.0% of the total end product is in the form of toluenediisocyanate residue which generally includes a combination of toluenediisocyanate ureas, carbodiimides and biurets as well as other by products. The amount of free isocyanate (NCO) is relatively low, i.e. 0.2% and free TDI is substantially nil. To recycle the toluenediisocyanate residues into useful products in accordance with the teachings of the present invention, the toluenediisocyanate residue is reacted at reflux with a primary amine and, more particularly, an alkanolamine such as monoethanolamine according to the following reaction:

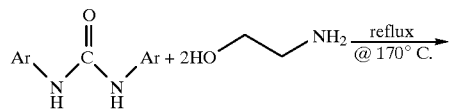

wherein Ar is an aromatic functional group.

The intermediary product obtained during reflux is thereafter distilled to obtain various products including, but not limited to, toluenediamine, oxazolidone and hydroxyethylimidiazolidone, among others.

To optimize the yield of one or more of the resulting products from the reaction of toluenediisocyanate residues with monoethanolamine (MEOA), it was determined that the amount of MEOA to mol. equivalents of TDI residue can be varied as exemplified in Table II shown below, which in turn has a corresponding effect on the amount of product recoverable and particularly, toluenediamine.

To analyze for optimization of the reaction products, the aforementioned reaction was carried out by charging a 200g samples of TDI residue (collected from BASF Corporation's TDI plant at Geismar, Louisiana) to separate 500 mL 3-neck round bottom flasks fitted with a thermowell, mechanical stirrer and reflux condenser. Variable amounts of monoethanolamine as set forth in Table I were added to each flask while stirring. The mixture was then heated to reflux at approximately 170° C. for ten hours. While the reaction was being carried out, small aliquots were withdrawn from each flask at four, six, eight and ten hours, respectively, for analysis by gas chromatography-fourier transform infrared radiation (GC/FTIR).

Additionally, at the end of the ten hour reaction period, samples were withdrawn from each flask, transferred to a single neck round bottom flask and distilled bulb to bulb in a Kugelrohr coffee pot style distillation apparatus with the contents of each distillation bulb being separately evaluated by gas chromatography-mass spectroscopy (GC/MS).

TABLE I

Quantities Used in TDI Residue - MEOA Reaction

| Experiment No. | 1 | 2 | 3 | 4 | 5 |
|---|---|---|---|---|---|
| wt TDI Residue | 200 | 200 | 200 | 200 | 200 |
| equiv TDI Residue | 2.3 | 2.3 | 2.3 | 2.3 | 2.3 |
| wt of MEOA | 100 | 150 | 200 | 300 | 350 |
| moles MEOA | 1.64 | 2.46 | 3.28 | 4.92 | 5.74 |
| moles MEOA/eq Residue | 0.7 | 1.1 | 1.4 | 2.1 | 2.5 |

As illustrated in Table II below, the amount of toluenediamine (TDA) recovered from the raw toluenediisocyanate residue as determined by both mass spectroscopy and fourier transform infrared radiation based on ten hour reaction samples ranged from 39% to approximately 58% based on the total weight of residue employed. The maximum yield of TDA appeared to occur when the molar ratio of TDI residue to MEOA was 1:1. Further, Table II demonstrates that the TDI residue yielded a maximum amount of oxazolidone, i.e. 9% at ratios of 1.3:1 and 1:1, respectively. Table II also illustrates that maximum yields of hydroxyethylimidiazolidone (HEID) were found at a ratio of 0.67:1. While it is not fully known why the amount of HEID as determined by mass spectroscopy varied at a ratio of 0.57:1, it is suspected that there may have been an error in injecting the sample into the gas spectroscopy-mass spectrometer (GC-MS).

TABLE II

Reaction of TDI residue with monoethanolamine

| Exp. | RES:AM[1] | % TDA GC-MS | % OXA[2] GC-MS | % HEID[3] GC-MS | % TDA GC-FTIR | % HEID GC-FTIR |
|---|---|---|---|---|---|---|
| 1 | 2:1 | 39 | 5 | 16 | 39 | 16 |
| 2 | 1.3:1 | 51 | 9 | 15 | 52 | 16 |
| 3 | 1:1 | 56 | 9 | 17 | 58 | 17 |
| 4 | 0.67:1 | 48 | 3 | 24 | 49 | 24 |
| 5 | 0.57:1 | 51 | 5 | 3 | 52 | 22 |

[1]RES:AM — the molar ratio of TDI residue to monoethanolamine
[2]OXA — oxazolidone
[3]HEID — hydroxyethylimidiazolidone While it will be apparent that the preferred embodiments of the invention disclosed are well calculated to fulfill the objects stated, it will be appreciated that the invention is susceptible to modification, variation and change without departing from the spirit thereof. For example, as should be understood by those skilled in the art where the TDI residue contains excess TDI, it is anticipated that the amount of TDA recovered in accordance with the teachings of the present invention will also be greater.

A greater appreciation of the invention will be gained upon review of the following claims.

what is claimed is:

1. A method for recycling toluenediisocyanate residue produced as a result of manufacturing toluenediisocyanate by the phosgenation of toluenediamine in the presence of a solvent consisting essentially of the steps of:
    a) treating toluenediisocyanate residue with an alkanolamine at reflux to produce an intermediary component, the treating occurring at a temperature of about 170° C., the intermediary component being selected from the group consisting of raw toluenediamine, oxazolidone, and hydroxyethylimidiazolidone; and
    b) distilling the intermediary component to obtain at least one product selected from the group consisting of toluenediamine, oxazolidone, and hydroxyethylimidiazolidone.

2. The method according to claim 1, wherein said alkanolamine is a monoethanolamine.

* * * * *